(12) United States Patent
Hill

(10) Patent No.: US 8,807,813 B2
(45) Date of Patent: Aug. 19, 2014

(54) RING LIGHT ILLUMINATOR AND BEAM SHAPER FOR RING LIGHT ILLUMINATOR

(75) Inventor: Andy Hill, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/376,249

(22) PCT Filed: Apr. 28, 2011

(86) PCT No.: PCT/IB2011/051867
§ 371 (c)(1),
(2), (4) Date: Dec. 5, 2011

(87) PCT Pub. No.: WO2011/135534
PCT Pub. Date: Nov. 3, 2011

(65) Prior Publication Data
US 2012/0087143 A1  Apr. 12, 2012

Related U.S. Application Data

(60) Provisional application No. 61/328,869, filed on Apr. 28, 2010.

(51) Int. Cl.
*G02B 6/32* (2006.01)
(52) U.S. Cl.
USPC .......................... 362/555; 362/244; 362/582

(58) Field of Classification Search
USPC .......... 362/237, 244, 551, 555, 558, 556, 582
See application file for complete search history.

(56) References Cited

U.S. PATENT DOCUMENTS

| | | | | |
|---|---|---|---|---|
| 4,883,333 A * | 11/1989 | Yanez | | 362/551 |
| 7,390,116 B2 * | 6/2008 | Jain | | 362/551 |
| 7,661,860 B2 * | 2/2010 | De Lamberterie | | 362/555 |
| 2004/0141336 A1 * | 7/2004 | West et al. | | 362/555 |
| 2004/0252281 A1 | 12/2004 | Fischer et al. | | |
| 2005/0174658 A1 | 8/2005 | Long et al. | | |
| 2008/0123052 A1 | 5/2008 | Su et al. | | |
| 2008/0210953 A1 * | 9/2008 | Ladstatter et al. | | 362/294 |

FOREIGN PATENT DOCUMENTS

| | | |
|---|---|---|
| CN | 2639704 Y | 9/2004 |
| CN | 1820216 A | 8/2006 |
| WO | 2005078505 A1 | 8/2005 |

* cited by examiner

*Primary Examiner* — Y My Quach Lee
(74) *Attorney, Agent, or Firm* — Suiter Swantz pc llo

(57) ABSTRACT

A ring light illuminator with annularly arranged light sources is disclosed. To each light source there corresponds a beam shaper comprising a light collector, a homogenizing means for light from the light source, and an imaging means for imaging an output of the homogenizing means into an area to be illuminated. The homogenizing means in embodiments is a rod, into which light from the light collector is directed. The end of the rod opposite the light collector is imaged by the imaging means into the area to be illuminated.

12 Claims, 10 Drawing Sheets

RING LIGHT ILLUMINATOR AND BEAM SHAPER FOR RING LIGHT ILLUMINATOR

CROSS REFERENCE TO RELATED APPLICATIONS

This patent application claims priority of US provisional patent application No. 61/328,869 filed Apr. 28, 2010, the application is incorporated herein by reference.

FIELD OF THE INVENTION

The present invention relates to a ring light illuminator. The present invention also relates to a beam shaper.

BACKGROUND OF THE INVENTION

In many optical inspection or imaging tasks a well-defined illumination of the area to be inspected or imaged is required. For many such illumination purposes ring lights are used, for example in microscopy, where they are a common means to provide a dark field illumination. In such applications, it is desirable to restrict the area illuminated to the area of interest, and to have a homogeneous distribution of light within the area of interest. Possible light sources for example are arc lamps, LEDs (light emitting diodes), laser diodes, and halogen bulbs. While arc lamps typically provide higher light intensities than LEDs, they also exhibit stronger intensity fluctuations and shorter life times than LEDs; thus generally LEDs are a preferred choice of light source. As light from typical LEDs is emitted into a hemisphere around the LED, optical elements are required to direct as much as possible of the emitted light from one or plural LEDs into the area of interest, i.e. into the area to be illuminated.

The European Patent Application EP 1 919 001 A1 relates to a spot light device for product inspection, wherein a LED is used as light source. In order to homogenize the distribution of light across a certain area, the light from the LED is passed through a rod lens. The light from the LED is introduced into the rod lens by a condensing lens. In order to assure proper alignment of rod lens and condensing lens, and also in order to reduce the number of individual parts to be handled during assembly of an optical system, the rod lens and condensing lens are provided as sections of an optical unit, the rod lens constituting a light transmitting section and the condensing lens a light condensing section. The condensing section combines refraction and reflection in order to direct light from the light source into the transmitting section.

The European Patent Application EP 2 177 816 A2 discloses an array of light sources, in particular LEDs, the light of which is directed into a light integrator shaped as a rod. The light integrator homogenizes and constrains the light, based on reflection of the light within the integrator. The light integrator may be a hollow tube with reflective inner surface or a solid rod of an optically transparent material, where the reflection of light within the light integrator is due to total internal reflection. The cross-section of the light integrator may be circular, polygonal, or irregular. Further optical elements may be provided downstream from the light integrator. To each of the light sources there may correspond an optical element for controlling and directing the light from the light source. The light integrator may be tapered, in order to influence the divergence of the light exiting from the light integrator.

The European Patent Application EP 1 150 154 A1 discloses an illumination system, in particular for microscopes, wherein plural light sources, preferentially LEDs, are arranged in an annular carrier. The LEDs may be controlled individually or in groups, and exhibit a small angle of emission.

The German Patent Application DE 28 52 03 discloses an illumination setup for a microscope, where light from a light source is guided along optical fibres and exits the fibres at a respective end of the fibres, wherein these respective ends are arranged in an annular fashion. A further ring illumination system, based on optical fibres is for example disclosed in the German patent application DE 40 16 264.

A problem of ring illumination systems based on optical fibres is the large divergence of the light exiting an optical fibre. Likewise, annular arrangements of LEDs tend to create rather inhomogeneous fields, and even if such LEDs are used in combination with state of the art collector lenses, the degree of homogeneity of the illumination field required for some applications is not achievable.

Maximum light intensity is a very important design parameter for ring lights, as these inherently are "dark field" illumination, where scattered light is often a viewing object. A main disadvantage of LEDs compared to arc lamps (a standard for bright illumination for normal microscope viewing), is that they are typically dimmer. It is often the case, that LED based systems do not provide adequate light intensity at the viewed object, and that extreme care in design should be made to maximize the possible light at the image. Maximizing the light is particularly important in machine vision/inspection where integration time cannot be arbitrarily lengthened to increase the light energy available to create a well exposed image. Increase of the integration time in a machine vision system decreases the frequency of images and increases the total inspection time (image time). Since the value of an inspection machine depends on how many fields can be imaged in a fixed time, maximizing the light at the object is a very important feature.

SUMMARY OF THE INVENTION

It is an object of the present invention to provide a ring light illuminator capable of creating a well-defined and homogeneous illumination field in an area to be illuminated. Additionally, light from ring illuminator should be collected efficiently and directed to the area to be illuminated.

This object is achieved by a ring light illuminator with a plurality of light sources, wherein to each light source there corresponds a beam shaper, the beam shaper comprising:
  a light collector for collecting light from a light source;
  a homogenizing means for light from the light source; and
  an imaging means for imaging an output of the homogenizing means into an area to be illuminated.

It is a further object of the invention to provide a beam shaper which is easily mounted and does not require alignment of its parts. Additionally, light from a light source should be collected efficiently and minimal truncation losses of an imaging lens should result.

This object is achieved by a beam shaper manufactured as one piece, comprising:
  a light collector for collecting light from a light source;
  a homogenizing rod for homogenizing the light from the light source; and
  a lens for imaging an end of the homogenizing rod opposite the light collector into an area to be illuminated.

The ring light illuminator according to the invention comprises a plurality of light sources arranged in an annular fashion. In preferred embodiments each light source is a light emitting diode (LED) or an array of LEDs. According to the invention, to each light source there corresponds a beam shaper. The beam shaper receives light from the light source and directs it into an area to be illuminated in such a way that an illumination field is created in the area to be illuminated, wherein the illumination field is of a well-defined shape and the illumination across the illumination field is homogeneous to a degree sufficient for the inspection or illumination task at hand.

The beam shaper comprises a light collector, a homogenizing means, and an imaging means.

The purpose of the light collector is to receive light from the light source and to direct it to the homogenizing means. The light collector preferentially is designed in such a way that an as large as possible fraction of the light emitted by the light source is collected by it and directed onto the homogenizing means, so that eventually an illumination field of sufficient intensity is achievable in the area to be illuminated.

The purpose of the homogenizing means is to reduce inhomogeneities of light intensity across the light beam, so that eventually the intensity of light across the illumination field is homogeneous to a sufficiently high degree.

The purpose of the imaging means is to image the output of the homogenizing means into the area to be illuminated. The size of the illumination field in part depends on the imaging properties of the imaging means.

In one preferred embodiment the homogenizing means is a rod of circular, elliptical, rectangular, square, hexagonal, octagonal or other cross-section; the cross-section herein is perpendicular to an optical axis of the beam shaper. The rod has a first end, through which light is received from the light collector, and a second end, opposite the first end along the optical axis, by which the light exits the rod. The second end of the rod is imaged into the area to be illuminated by the imaging means. The shape of the illumination field created in this way is determined by the cross section of the rod. The homogenizing function of the rod is due to reflection, typically multiple reflection, of light from the sides of the rod parallel to the optical axis. Preferentially, the rod is a solid piece of matter, transparent at least for the wavelengths of light to be used for illumination, and the reflection is total internal reflection. Alternatively, the sides of the rod can be provided with a reflective coating, or the rod can be a hollow tube with reflective inner walls. A benefit of the invention is that it combines collection efficiency of TIR lens and minimal truncation losses of the imaging lens of the beam shaper.

Advantageously, the rod and the light collector form an integral unit, and in particular may be manufactured as one piece. This reduces the number of individual parts which need to be handled in assembly or maintenance of the ring light illuminator, and also obviates the need to properly align the light collector and the rod during assembly or maintenance. Even more advantageously, light collector, rod, and imaging means form an integral unit and may be manufactured as one piece.

In some embodiments the imaging means is a lens.

In alternative embodiments, the homogenizing means is a texture provided on the light collector.

As the operation of the light sources generates heat, advantageously a cooling mechanism for the ring light illuminator is provided. In embodiments, this cooling mechanism comprises cooling fins provided on the outer surface of the ring light illuminator, so that the surface for heat exchange with the environment of the ring light illuminator is increased.

A beam shaper according to the invention, which may be used in a ring light illuminator according to the invention, but may also be employed for other purposes, is manufactured as one piece, so that the need to properly align plural parts of a beam shaper during assembly of an optical system is obviated. Also, the number of parts that need to be handled is reduced in this way. The beam shaper is made of a material which is transparent for the light wavelengths the beam shaper is to be used for. In embodiments, such a material can for example be a plastic material or glass.

One possibility of the molding material for the beam shaper is acrylic, another one would be polycarbonate. Acrylic has better transmission than polycarbonate but is less capable of withstanding elevated temperatures. Acrylic should be ok for applications where the illumination source does not produce a lot of excess heat. The transmission losses in acrylic are roughly 0.25% per mm which results in a 15% loss in case the beam shaper has an overall length of 67 mm.

The beam shaper according to the invention comprises a light collector, configured to collect light from a light source used with the beam shaper. The beam shaper also comprises a homogenizing rod, which is directed along an optical axis of the beam shaper. The light collector is arranged to direct the light it collected into the rod through a first end of the rod. The rod effects a homogenization of the light passed through it by reflection, typically multiple reflection, of the light from the sides of the rod. The reflection is total internal reflection. The beam shaper furthermore comprises a lens, which images a second end of the rod opposite the first end into an area to be illuminated.

A cross section of the rod perpendicular to the optical axis of the beam shaper in embodiments may be circular, elliptical, triangular, square, rectangular, hexagonal, octagonal or of any other shape.

The invention can be implemented in a microscope assuring a well-defined illumination, in particular of the dark field type, of an area inspected with the microscope. A microscope comprises at least one ring light illuminator according to the invention as described above. The beam shapers used in the at least one ring light illuminator can be of the one piece type according to the invention described above, but may alternatively comprise a light collector, homogenizing means and imaging means provided as more than one piece.

BRIEF DESCRIPTION OF THE DRAWINGS

The nature and mode of operation of the present invention will now be more fully described in the following detailed description of the invention taken with the accompanying drawing figures, in which

FIG. 10b is another perspective view of the light collector and the homogenizing rod of FIG. 10a;

DETAILED DESCRIPTION OF THE INVENTION

Figure 1A:
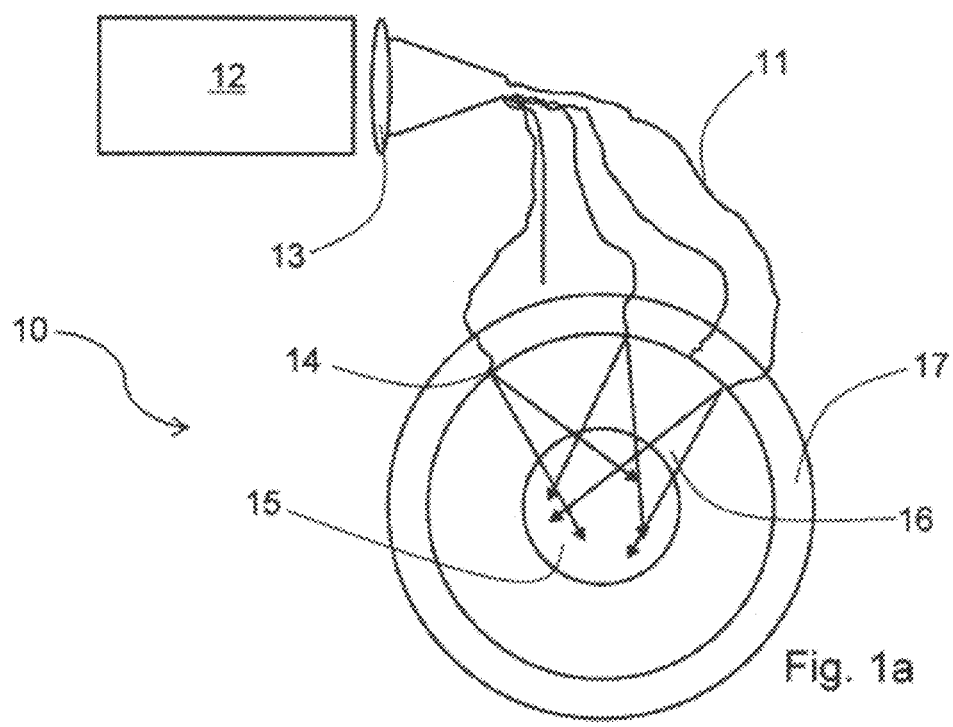
FIG. 1a shows a prior art ring light illuminator with annularly arranged ends of optical fibres.

Same reference numerals refer to same elements throughout the various figures. Furthermore, only reference numerals necessary for the description of the respective figure are shown in the figures. The shown embodiments represent only examples of how the invention can be carried out. This should not be regarded as limiting the invention.

FIG. 1a shows a setup for a prior art ring light illuminator 10. An arc lamp 12 is used as a light source; light from the arc lamp 12 is coupled into plural optical fibres 11 by suitable optical elements 13 (only one such element is shown in the drawing). Ends 14 of the optical fibres 11 are arranged annularly in a ring shaped carrier 17 of the ring light illuminator 10, in such a way that they emit the light from the arc lamp 12 towards an area 15 to be illuminated circumscribed by the carrier 17. As is indicated by the cones 16, the light is emitted from the ends 14 with a considerable divergence, meaning a divergence too large for many precision applications.

Figure 1B:
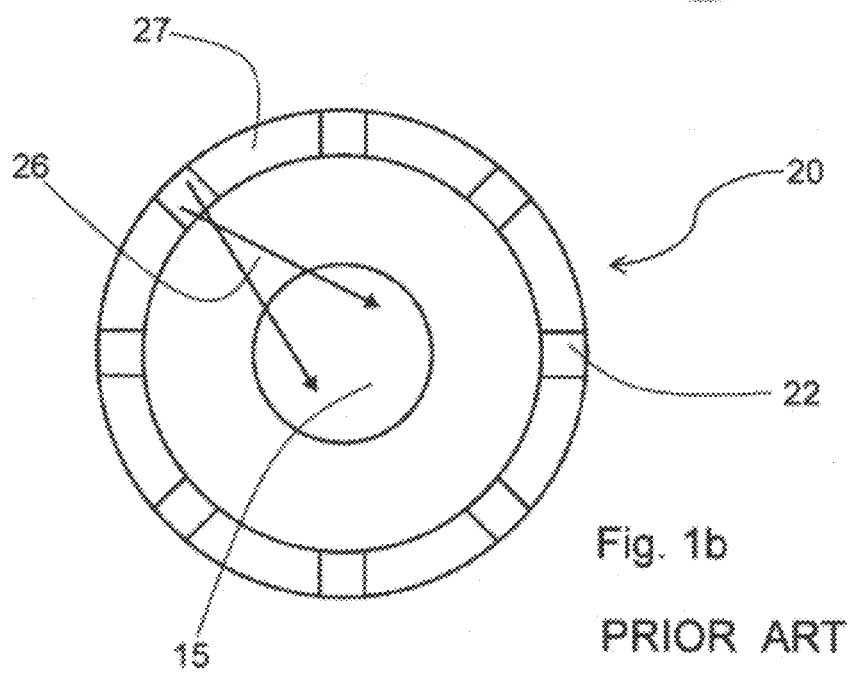
FIG. 1b shows a prior art ring light illuminator with annularly arranged light sources.

FIG. 1b shows another setup for a prior art ring illuminator 20. In an annular carrier 27 plural light sources 22 are arranged in an annular fashion. The light sources 22 emit light towards an area 15 to be illuminated. The light sources are LEDs, which typically are provided with shaping optics (not shown) to concentrate the light emitted from the LEDs around a predefined direction. As indicated by the cone 26, despite the shaping optics the light from a single light source exhibits a divergence that is too large for many precision applications. A ring light illuminator according to the invention has the same general setup as the prior art ring light illuminator shown; however, the prior art shaping optics are replaced with beam shapers according to the invention, of a configuration described below.

Figure 2:
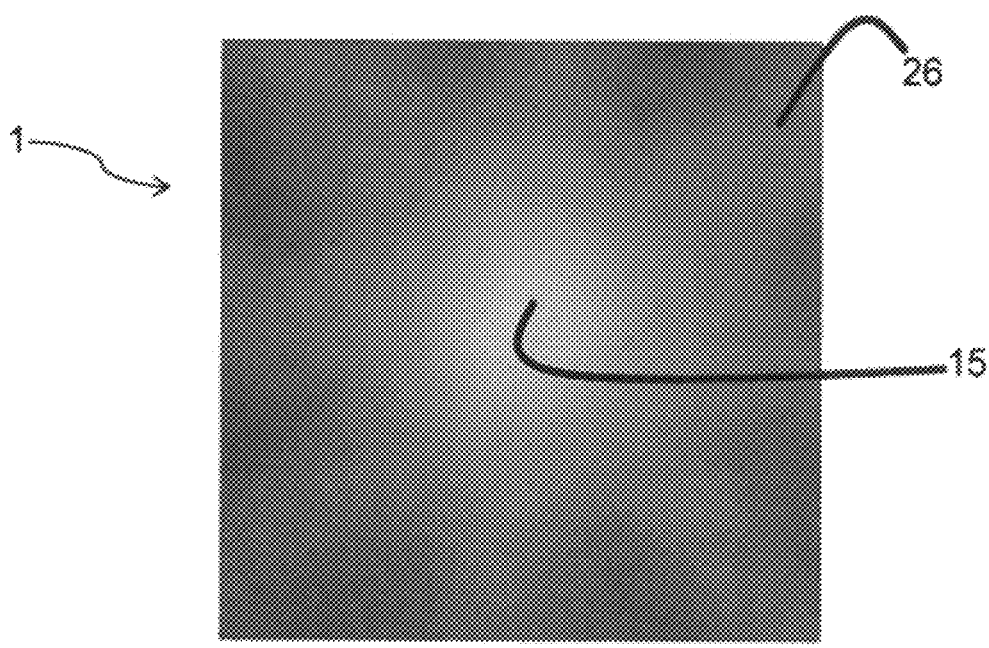
FIG. 2 shows the intensity distribution achievable with a prior art ring light illuminator as shown in FIG. 1b.

FIG. 2 shows the intensity distribution 1 achievable with a ring illuminator 20 as described in the context of FIG. 1b, comprising eight light sources with TIR lenses (see FIG. 3) as shaping optics. The illumination pattern is rather diffuse. The central region of the image shown is only moderately brighter than the regions illuminated by one of the cones 26, indicating that a considerable amount of intensity is directed towards off-centre regions of the area shown in the image rather than towards the central area 15 to be illuminated. The intensity distribution achievable with a ring illuminator 10 as described in the context of FIG. 1a is similar.

Figure 3:
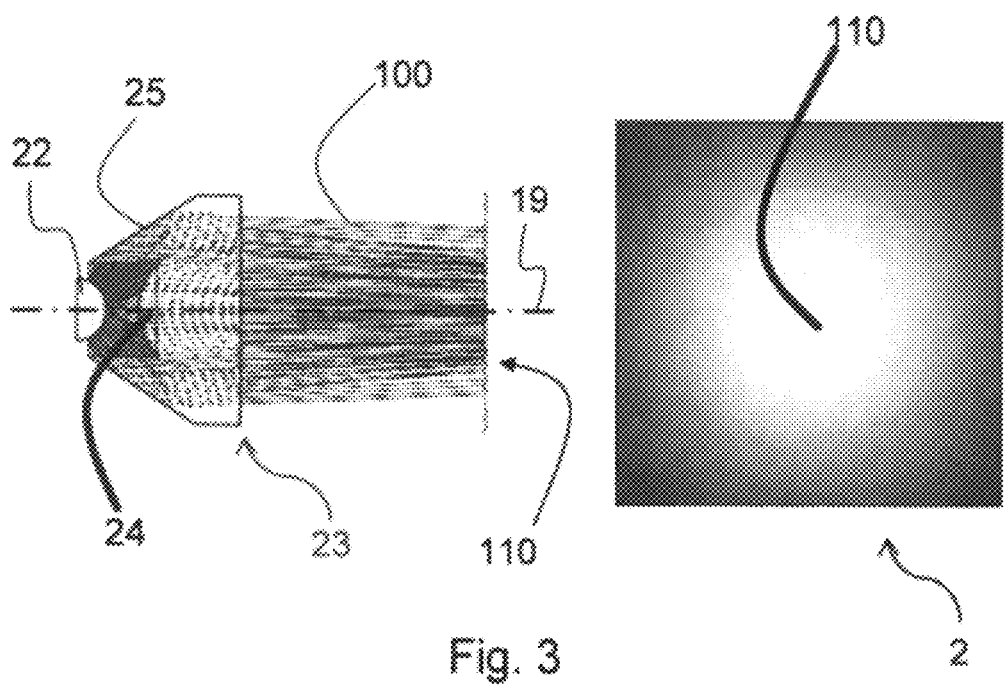
FIG. 3 shows a TIR lens and light rays as well as the intensity distribution created by it on a surface.

FIG. 3 shows a TIR (total internal reflection) lens 23. Light, indicated by light rays 100, from a light source 22, which here is an LED, is captured by the TIR lens 23 and directed towards a spot 110. Directing the light is achieved by two principles: A refractive lens portion 24 occupying a central part of the TIR lens 23 directs light rays 100 towards the spot 110 by refraction. Light rays 100 not hitting the refractive lens portion 24, but captured by the TIR lens 23, are directed towards the spot 110 by total internal reflection from a side surface 25 of the TIR lens 23. Also shown in FIG. 3 is the intensity distribution 2 of the spot 110 on a surface perpendicular to an optical axis 19 of the TIR lens 23. The intensity distribution 2 created by the TIP lens 23 is roughly Gaussian, so that there is maximum intensity in the centre of the spot 110, but there are also wide regions around the centre in which the intensity tails off, i.e. there are no clearly defined edges of the spot 110. A TIR lens 23 as described here can be used as shaping optics for a prior art ring illuminator 20 as described in the context of FIG. 1b. The intensity distribution 2 of the spot 110 without clearly defined edges is the reason why the intensity distribution 1 created by a cooperation of eight such combinations of light source 22 and TIR lens 23 is rather diffuse, as is evident from FIG. 2.

Figure 4:
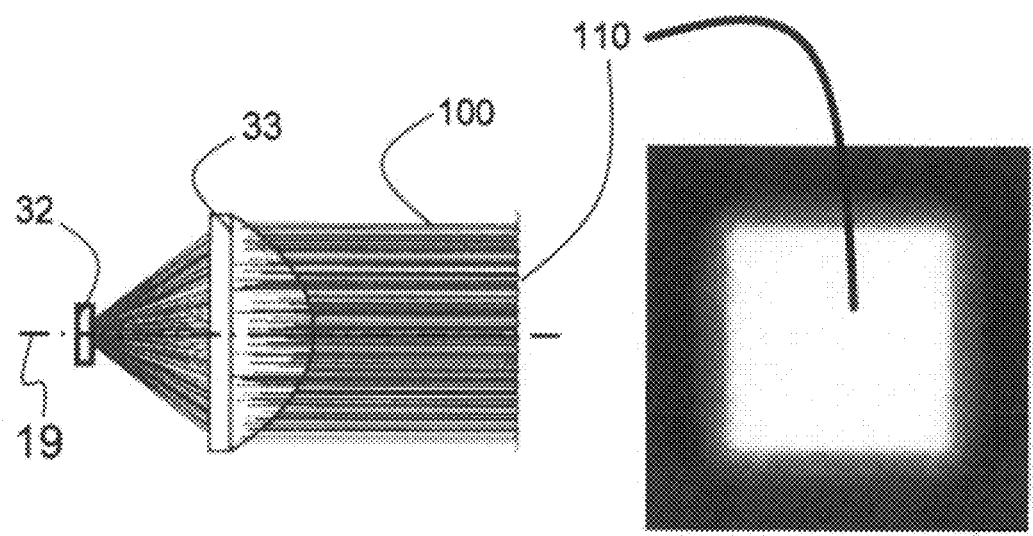
FIG. 4 shows an aspheric condenser lens and light rays as well as the intensity distribution created by it on a surface.

FIG. 4 shows an aspheric condenser lens 33 and light rays 100. As light source in this figure an emitter 32 of an LED is shown schematically. The aspheric condenser lens 33 captures light from the light source and directs it onto a spot 110. Also shown in FIG. 4 is the intensity distribution 3 of the spot 110 on a surface perpendicular to an optical axis 19 of the condenser lens 33, which is an image of the LED light emitter 32. Directly imaging the LED emitter 32 as in this case introduces high non-uniformity risks of the illumination of spot 110. Therefore the homogeneity of the intensity distribution created in an area to be illuminated by a ring light illuminator 20 of the type shown in FIG. 1b, with LEDs as light sources and aspheric condenser lenses 33 as shaping optics is not guaranteed to be sufficient for precision applications. Furthermore, typically the light collection efficiency of an aspheric condenser lens 33 as shown in FIG. 4 is lower than the light collection efficiency of a TIR lens 23 as shown in FIG. 3.

Figure 5:
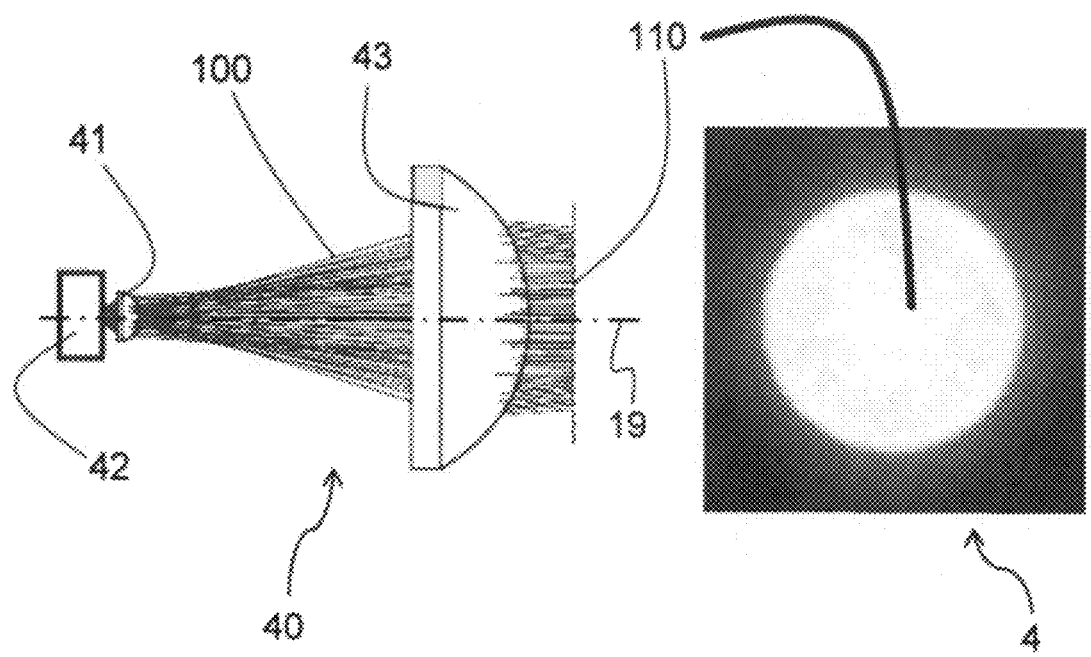
FIG. 5 shows a compound lens and light rays as well as the intensity distribution created by it on a surface.

FIG. 5 shows a compound lens 40 comprising a hemisphere lens 41 to collect light, indicated by light rays 100, from a light source 42, and a relay lens 43, which directs the light onto a spot 110. Also shown in FIG. 5 is the intensity distribution 4 of the spot 110 on a surface perpendicular to an optical axis 19 of the compound lens 40, which is an image of the flat back surface of the hemisphere lens 41, which is facing the light source 42. Such a setup has a lower light collection efficiency than a TIR lens 23 as described in FIG. 3, and is incompatible with encapsulated LEDs, which is a disadvantage in the assembly of an optical system like the ring light illuminator 20 of FIG. 1b.

Figure 6:
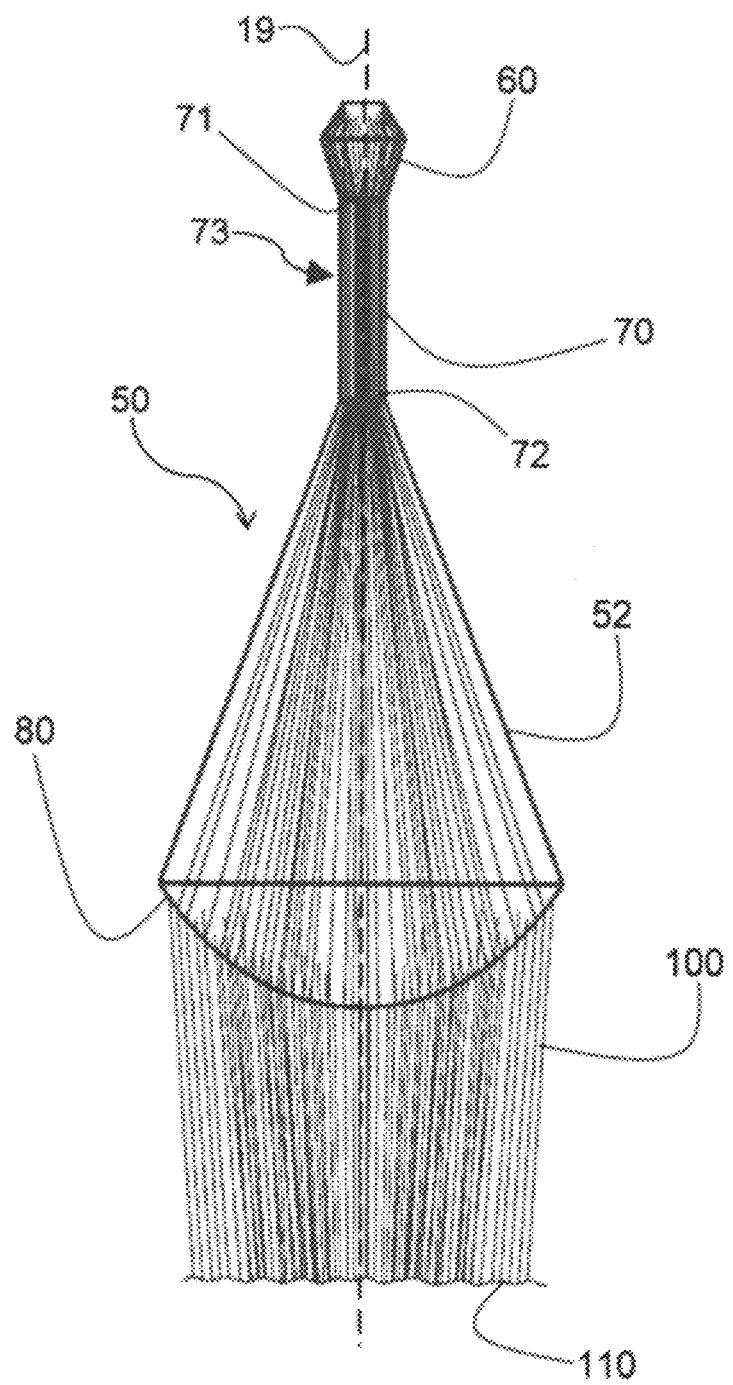
FIG. 6 shows a beam shaper according to the invention and light rays.

FIG. 6 shows a beam shaper 50 comprising a light collector 60, a homogenizing rod 70, a cone section 52, and a lens 80. A light source (not shown) is inserted in the light collector 60 and emits light indicated by the light rays 100. The light collector 60 collects light from the light source and directs it into the homogenizing rod 70, through a first end 71 of the homogenizing rod 70. In the homogenizing rod 70 the light is homogenized by reflection, typically multiple reflection, from the side surfaces 73 of the homogenizing rod. The beam shaper 50 is manufactured as one piece from a material that is transparent for the wavelengths of light the beam shaper is intended to be used with, like for example a plastic material or glass, and the reflection from the side surfaces 73 is total internal reflection. The light exits the homogenizing rod 70 through a second end 72 of the homogenizing rod 70, and enters the cone section 52. From there it reaches the lens 80, which directs the light onto a spot 110. The intensity distribution of the spot 110 is an image of the second end 72 of the homogenizing rod 70. The purpose of the cone section 52 is to establish a fixed distance between the second end 72 of the homogenizing rod 70 and the lens 80. As the beam shaper 50 is manufactured as one piece, no alignment of individual components, i.e. of light collector 60, homogenizing rod 70, and lens 80, is necessary during assembly of an optical system. This simplifies handling of the beam shaper 50, and the assembly of optical systems, like for instance a ring light illuminator 20, of the type shown in FIG. 1b; contrary to prior art, however, beam shapers 50 just discussed, rather than TIR lenses, are used as shaping optics in embodiments of ring light illuminators according to the invention. The beam shaper 50 can of course also be used for other illumination tasks and is not limited to ring light illumination.

Figure 7:
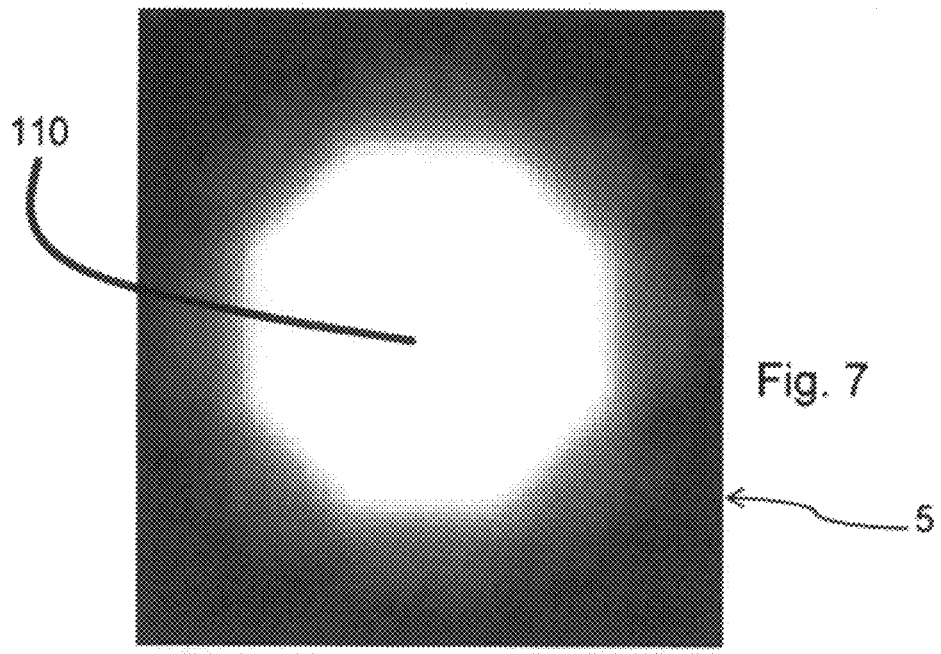
FIG. 7 shows the intensity distribution created on a surface by the beam shaper of FIG. 6.

FIG. 7 shows the intensity distribution 5 of the spot 110 created by the beam shaper 50 of FIG. 6 on a surface perpendicular to an optical axis 19 of the beam shaper 50. The shape of the spot 110 is determined by the cross section of the homogenizing rod 70, more precisely its cross section at the second end 72. In the embodiment shown, this cross section has an octagonal shape. As has already been mentioned, different shapes of the cross section are also possible. It should be noted that the spot 110 exhibits clearly defined edges, and, due to the effect of the homogenizing rod 70, the illumination intensity across the spot 110 is sufficiently homogeneous even for high precision applications.

Figure 8:
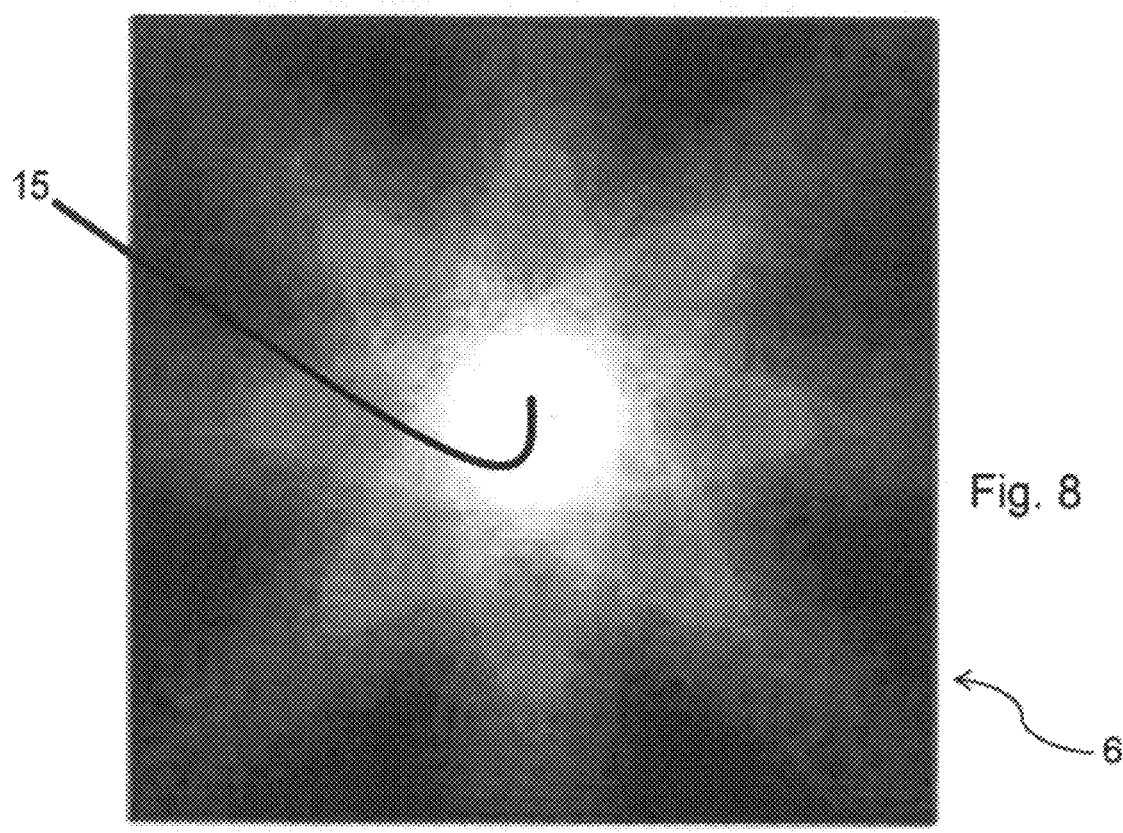
FIG. 8 shows the intensity distribution achievable with a ring light illuminator according to the invention.

FIG. 8 shows the intensity distribution 6 achievable with a ring illuminator according to the invention, which, in the embodiment this figure relates to, comprises eight beam shapers 50 of the type described in the context of FIG. 6 as shaping optics. This figure should be compared with FIG. 2. Due to the clearly defined edges of the light beams created by the beam shapers 50, which result in the clearly defined edges of the spots 110 shown in FIG. 7, in FIG. 8, the area 15 to be illuminated is distinctly brighter than its surroundings.

Figure 9:
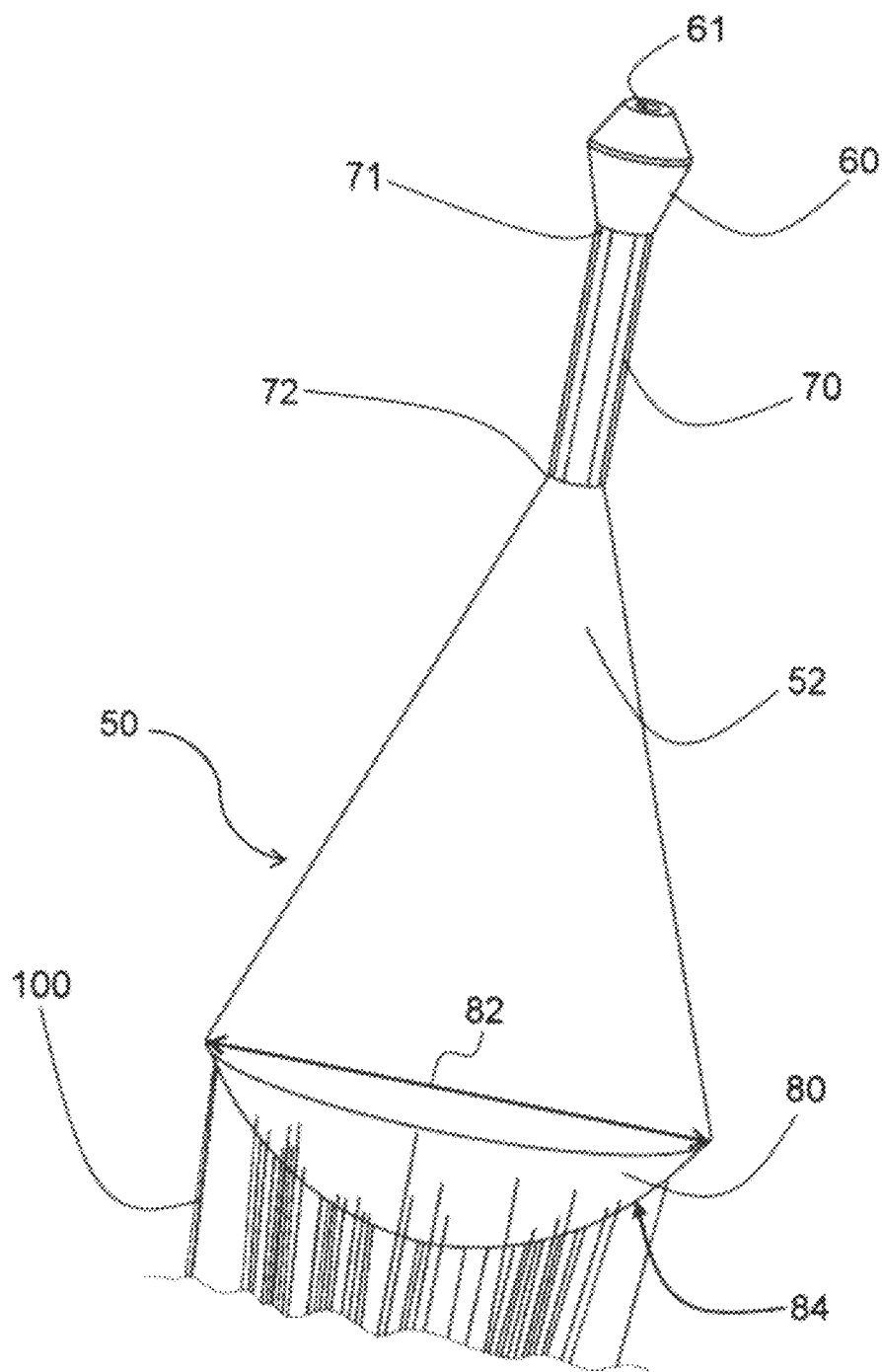
FIG. 9 is a perspective view of a beam shaper according to the invention.

FIG. 9 shows a perspective view of a beam shaper 50 according to the invention, as has already been shown in FIG. 6. Here light rays 100 exiting the lens 80 are shown. The configuration of such a beam shaper 50 has already been discussed in the context of FIG. 6. The light collector 60 exhibits a cavity 61 into which a light source (not shown) is to be introduced. The general configuration of the light collector 60 corresponds to that of a TIR lens 23, as shown in FIG. 3. The diameter 82 of lens 80 for imaging regulates the number of beam shapers 50 arranged in the ring-illuminator 20. The lens 80 has an exit surface 84 that images the light exiting the homogenizing rod 70 through the second end 72 of the homogenizing rod 70 onto a spot 110. It is recommended that the exit surface 84 of the lens 80 for imaging is aspheric.

Figure 10A:
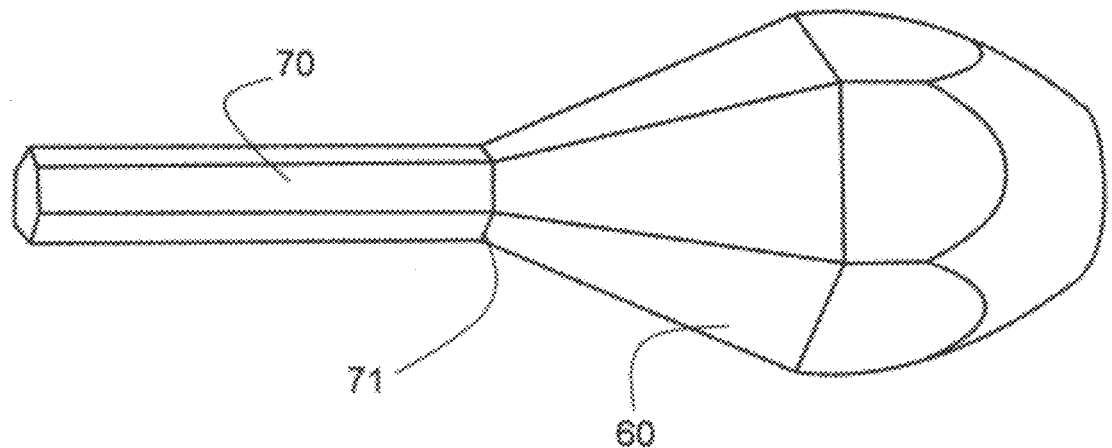
FIG. 10a is a perspective view of a light collector and a homogenizing rod.
Figure 10B:
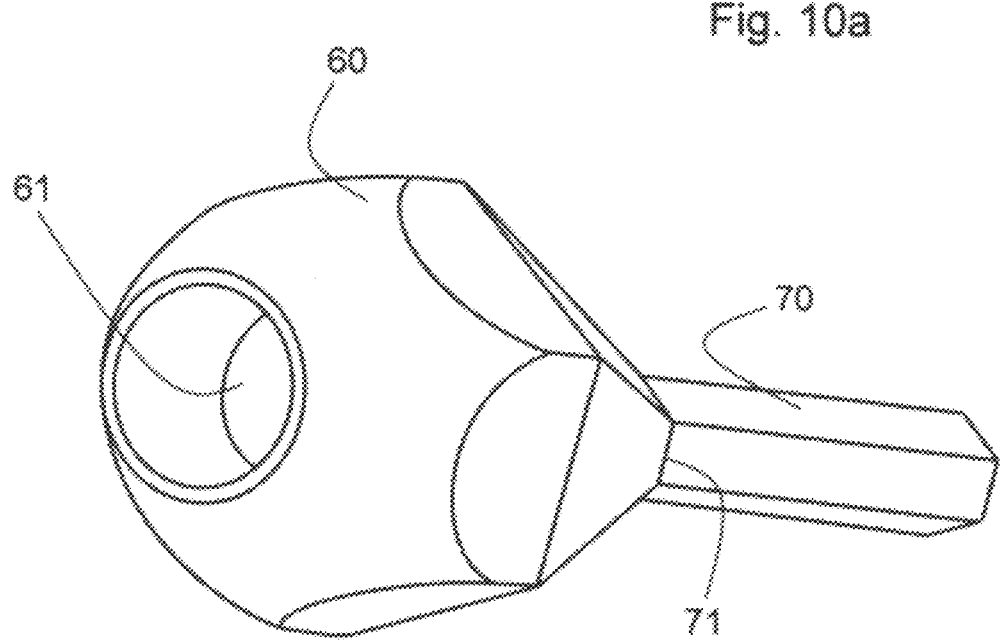

FIGS. 10a and 10b are perspective views of a light collector 60 as used for a beam shaper 50 according to the invention, as shown in FIGS. 6 and 9, as well as in shaping optics for a ring light illuminator according to the invention, which may be composed of several pieces. Only a part of the homogenizing rod 70 attached to the light collector 60 is shown. The rod 70 here has a hexagonal cross section, and the shape of the light collector 60 is adapted to the cross section of the rod 70, also exhibiting a hexagonal cross section in a section adjacent to the first end 71 of the rod 70. FIG. 10b clearly shows the cavity 61 of the light collector 60, into which a light source (not shown), typically an LED, is to be inserted.

Figure 11:
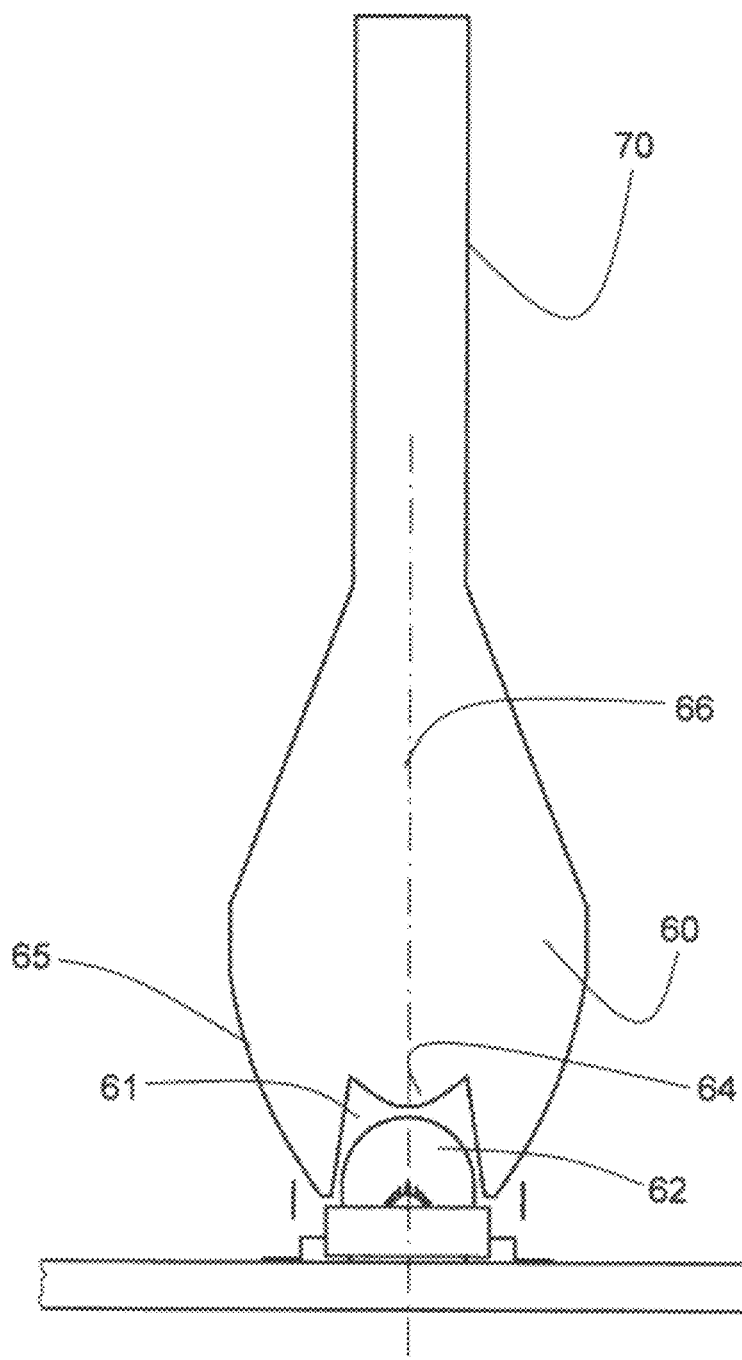
FIG. 11 shows a light source introduced into a cavity in a light collector with a homogenizing rod.

FIG. 11 shows a sectional view of a light collector 60 and part of a homogenizing rod 70. A LED 62 is introduced in the cavity 61 of the light collector 60. Analogous to the 70 lens 23 of FIG. 3, the light collector 60 exhibits a refractive lens portion 64, which collects light emitted into a central region around an optical axis 66. The cross section of this region is determined by the shape and size of the refractive lens portion 64. Light emitted by the LED into a region outside the central region is directed into the homogenizing rod 70 by total internal reflection from a side surface 65 of the light collector 60.

Figure 12:
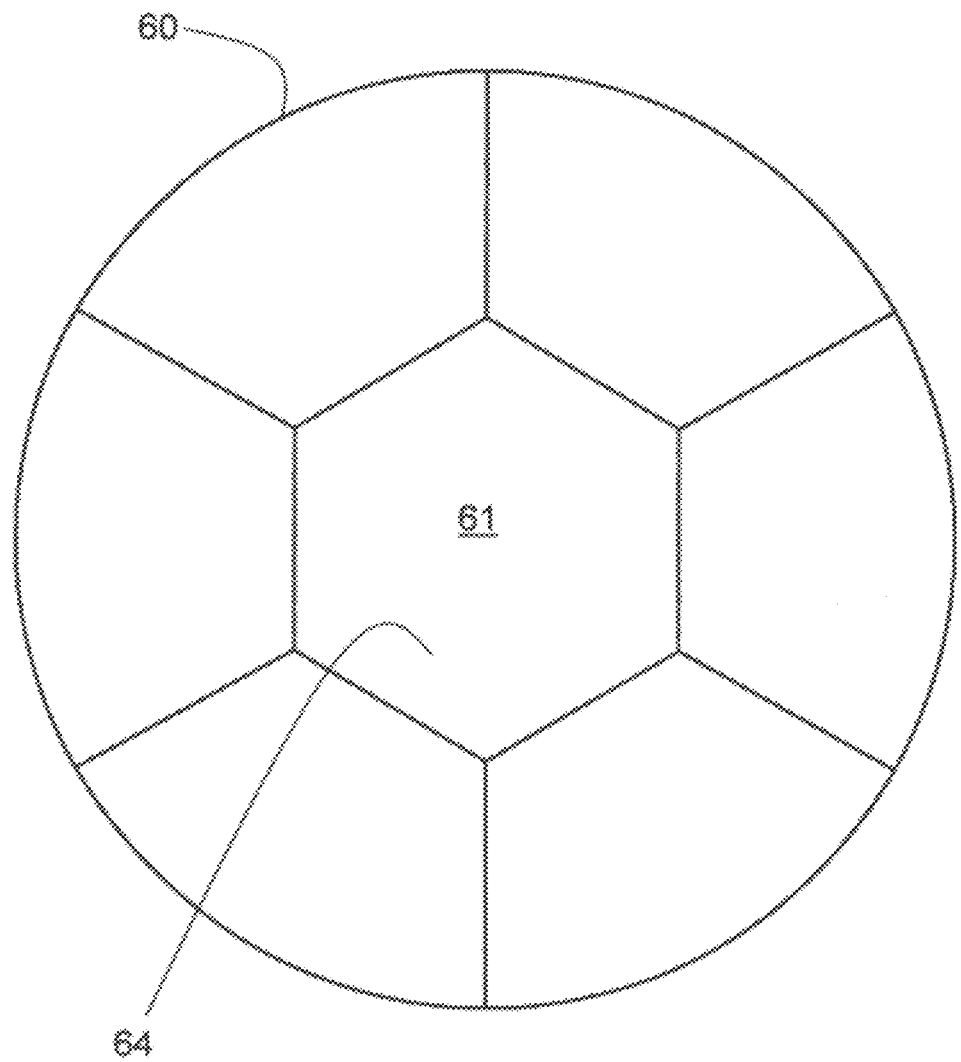
FIG. 12 is a top view of the cavity in a light collector.

FIG. 12 is a top view of the cavity 61 in a light collector 60, into which a light source like the LED 62 in FIG. 11 is to be inserted. The cavity 61 and the refractive lens portion 64 have an hexagonal cross section.

Figure 13:
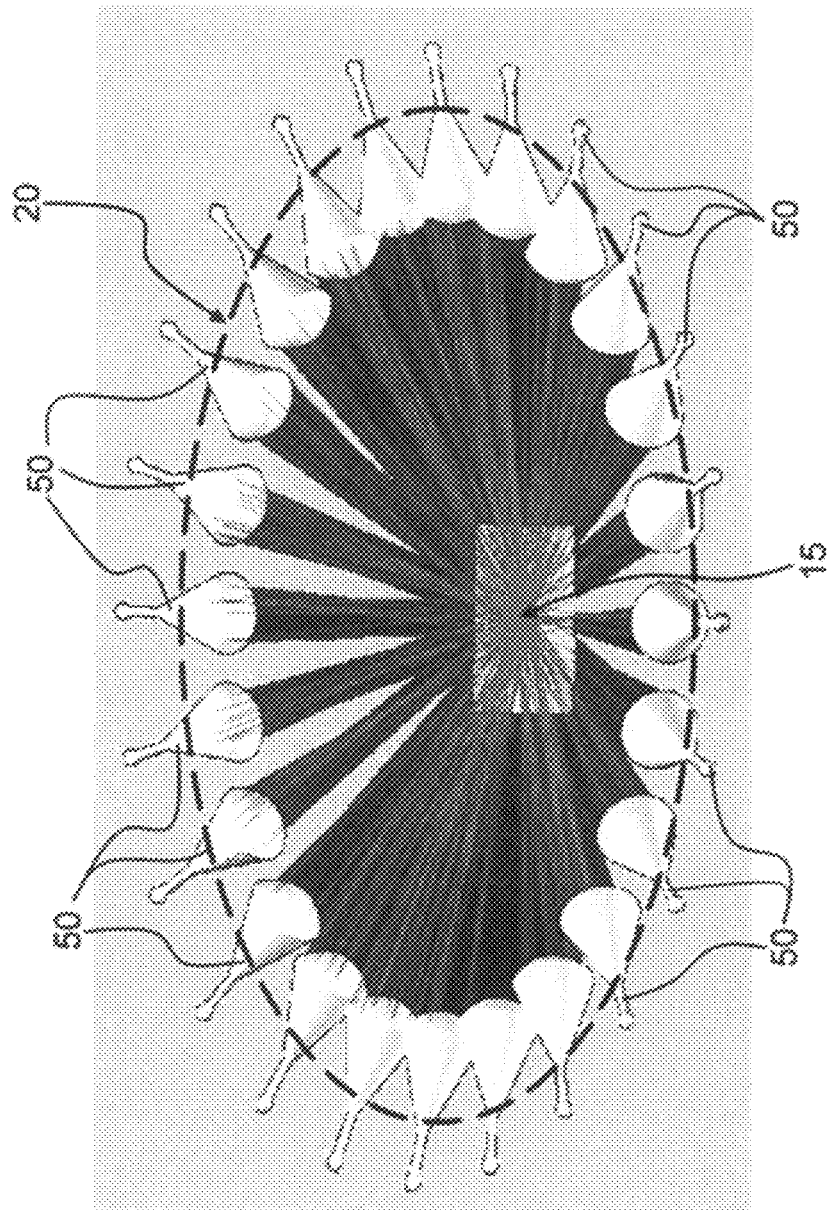
FIG. 13 is an embodiment of a possible implementation of a plurality of beam shapers arranged in ring to constitute the ring-illuminator according to the invention.

FIG. 13 is an embodiment of a possible implementation of a plurality of beam shapers 50 arranged in ring to form the ring-illuminator 20 according to the invention. The plurality of beam shapers 50 arranged in the ring-illuminator 20 provides a homogeneous illumination for the area 15 to be illuminated. The diameter 82 of lens 80 (sec FIG. 9) regulates the number of beam shapers 50 arranged in the ring-illuminator 20. In the embodiment shown here, the diameter 82 of lens 80 is 30 mm, which results in approximately 24 beam shapers 50 arranged in the ring-illuminator 20.

The invention has been described with reference to specific embodiments. It is obvious to a person skilled in the art, however, that alterations and modifications can be made without leaving the scope of the subsequent claims.

REFERENCE NUMERALS 1, 6 intensity distribution
2, 3, 4, 5 intensity distribution
10, 20 ring light illuminator
11 optical fibre
12 arc lamp
13 optical element
14 end of optical fibre
15 area to be illuminated
16, 26 cone of light
17, 27 earner
19, 66 optical axis
22, 42 light source
23 TIR lens
24, 64 refractive lens portion
25, 65 side surface
32 LED emitter
33 aspheric condenser lens
40 compound lens
41 hemisphere lens
43 relay lens
50 beam shaper
52 cone section
60 light collector
61 cavity
62 LED
70 homogenizing rod
71 first end of homogenizing rod
72 second end of homogenizing rod
73 side surface of homogenizing rod
80 lens
82 diameter of lens
84 exit surface
100 light ray
110 spot

What is claimed is:

1. A ring light illuminator comprising:
a plurality of annularly arranged light sources;
a plurality of beam shapers, each beam shaper assigned to a light source of the plurality of annularly arranged light sources, wherein each beam shaper includes:
a light collector for collecting light from the assigned light source, wherein the light collector includes a receiving cavity and a refractive lens portion, wherein the cavity of the light collector is arranged to encompass the assigned light source, wherein the light collector has a polygonal cross-section;
a homogenizer optically coupled to an output of the light collector and configured to homogenize light from the assigned light source; and an imaging lens for imaging an output of the homogenizer into an area to be illuminated, wherein the homogenizer has a polygonal cross-section matched to the polygonal cross-section of the light collector.

2. The ring light illuminator according to claim 1, wherein the homogenizer is a rod.

3. The ring light illuminator according to claim 2, wherein the rod and the light collector together form a one-piece unit.

4. The ring light illuminator according to claim 2, wherein the rod, the light collector and the imaging lens together form a one-piece unit.

5. The ring light illuminator according to claim 2, wherein a homogenizing function of the rod is based on total internal reflection of light within the rod.

6. The ring light illuminator according to claim 1, wherein the imaging lens has an aspheric exit surface.

7. The ring light illuminator of claim 1, wherein each light source comprises at least one light emitting diode (LED).

8. The ring light illuminator of claim 1, wherein the ring light illuminator includes a plurality of cooling fins.

9. A beam shaper comprising:
a light collector for collecting light from a light source, wherein the light collector includes a receiving cavity and a refractive lens portion, wherein the cavity of the light collector is arranged to encompass the light source, wherein the light collector has a hexagonal cross-section;
a homogenizing rod for homogenizing the light from the light source; and
a lens for imaging an end of the homogenizing rod opposite the light collector into an area to be illuminated, wherein the light collector, the homogenizing rod and the lens for imaging manufactured as one piece, wherein the homogenizer has a hexagonal cross-section matched to the hexagonal cross-section of the light collector.

10. The beam shaper of claim 9, wherein the beam shaper is molded from a plastic material.

11. The beam shaper of claim 9, wherein the beam shaper is made of glass.

12. The beam shaper of claim 9, wherein the lens for imaging has an aspheric exit surface for imaging the homogenizing rod onto an area to be illuminated.

* * * * *